United States Patent [19]
Yanagisawa et al.

[11] Patent Number: 6,140,523
[45] Date of Patent: *Oct. 31, 2000

[54] ORGANOSILICON COMPOUNDS AND MAKING METHOD

[75] Inventors: Hideyoshi Yanagisawa; Masaaki Yamaya, both of Gunma-ken, Japan

[73] Assignee: Shin-Etsu Chemical Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/472,895

[22] Filed: Dec. 28, 1999

[30] Foreign Application Priority Data

Jan. 12, 1999 [JP] Japan .................................. 11-004917

[51] Int. Cl.⁷ ....................................................... G07F 7/10
[52] U.S. Cl. .............................................. 556/422; 544/69
[58] Field of Search ................................ 556/422; 544/69

[56] References Cited

U.S. PATENT DOCUMENTS 5,426,205  6/1995  Kirchmeyer et al. .................... 556/422
5,663,358  9/1997  Cohen et al. .

FOREIGN PATENT DOCUMENTS 925362  1/1997  Japan .

*Primary Examiner*—Paul F. Shaver
*Attorney, Agent, or Firm*—Birch, Stewart, Kolasch & Birch, LLP

[57] ABSTRACT

Novel organosilicon compounds containing organooxysilyl and sulfenamide groups in the molecule are provided. They are useful as interfacial binders between inorganic materials and organic materials, adhesion modifiers for organic resins and rubber, primers, etc.

2 Claims, 6 Drawing Sheets

ORGANOSILICON COMPOUNDS AND MAKING METHOD

This invention relates to novel organosilicon compounds containing organooxysilyl and sulfenamide groups in the molecule and a method for preparing the same.

BACKGROUND OF THE INVENTION

Compounds containing alkoxysilyl and mercapto groups in the molecule as typified by mercaptopropyltrimethoxysilane are known in the art. These compounds are useful as interfacial binders between inorganic materials such as silica, aluminum hydroxide and talc and organic materials such as thermosetting resins, thermoplastic resins and rubber, adhesion modifiers for organic resins and rubber, primers, etc.

Although the mercapto-bearing organosilicon compounds are applied to composite systems composed of resins or rubber and inorganic materials, these organosilicon compounds suffer from the problem that when a resin or rubber having a mercapto-bearing organosilicon compound added is mixed with an inorganic material, mercapto groups react with the resin or rubber so that the resin or rubber cures prior to molding.

SUMMARY OF THE INVENTION

An object of the invention is to provide a novel organosilicon compound having solved the above problem. Another object of the invention is to provide a method for preparing the novel organosilicon compound.

The invention is predicated on the following discovery. By reacting an amino-bearing compound of the general formula (2) with an alkali hypochlorite aqueous solution, separating an aqueous layer from the reaction solution, and further reacting the reaction product with a mercapto-bearing organosilicon compound of the general formula (3) according to the reaction scheme shown below, there is obtained a novel organosilicon compound having organooxysilyl and sulfenamide groups of the general formula (1) shown below. This novel organosilicon compound is useful as interfacial binders between inorganic materials and organic materials (e.g., thermosetting resins, thermoplastic resins and rubber), adhesion modifiers for organic resins and rubber, primers, etc. In such an application involving mixing of a resin or rubber with an inorganic material, the organosilicon compound does not cause the resin or rubber to cure during mixing.

In the formulae, $R^1$ is a monovalent hydrocarbon group of 1 to 4 carbon atoms, $R^2$ is a divalent hydrocarbon group of 1 to 10 carbon atoms, $R^3$ is hydrogen or a monovalent hydrocarbon group of 1 to 10 carbon atoms, $R^4$ is a monovalent hydrocarbon group of 1 to 10 carbon atoms, or $R^3$ and $R^4$, taken together with the nitrogen atom, form an alicyclic structure of 4 to 10 carbon atoms which may be separated by an oxygen atom, n is equal to 1, 2 or 3, and M is an alkali metal.

Accordingly, the invention in a first aspect provides an organosilicon compound of formula (1). In a second aspect, the invention provides a method for preparing an organosilicon compound of formula (1) comprising the steps of reacting an amino-bearing compound of formula (2) with an aqueous solution of an alkali hypochlorite, separating an aqueous layer from the reaction solution, and further reacting the reaction product with a mercapto-bearing organosilicon compound of formula (3).

DESCRIPTION OF THE PREFERRED EMBODIMENTS

The organosilicon compounds of the invention are of the general formula (1).

Herein, $R^1$ is a monovalent hydrocarbon group of 1 to 4 carbon atoms, $R^2$ is a divalent hydrocarbon group of 1 to 10 carbon atoms, and n is equal to 1, 2 or 3 and preferably equal to 2 or 3. Illustrative of $R^1$ are alkyl groups such as methyl, ethyl, n-propyl, isopropyl and n-butyl and alkenyl groups such as vinyl and allyl, with the alkyl groups being preferred. Illustrative of $R^2$ are alkylene groups such as methylene, ethylene, propylene, n-butylene, isobutylene, hexylene, and decylene, arylene groups such as phenylene, and aralkylene groups such as methylphenylethylene. Of these, alkylene groups of 1 to 6 carbon atoms are preferred, with propylene being especially preferred.

$R^3$ is hydrogen or a monovalent hydrocarbon group of 1 to 10 carbon atoms. $R^4$ is a monovalent hydrocarbon group of 1 to 10 carbon atoms. Examples of the monovalent $C_{1-10}$ hydrocarbon group include alkyl groups such as methyl, ethyl, n-propyl, isopropyl, n-butyl, isobutyl, t-butyl, hexyl, cyclohexyl, and octyl, aryl groups such as phenyl, and aralkyl groups such as benzyl.

Alternatively, $R^3$ and $R^4$, taken together, form with the nitrogen atom an alicyclic structure of 4 to 10 carbon atoms which may be separated by an oxygen atom. In this case, the compounds of formula (1) are represented by the following general formula (1'):

(1')

wherein $R^5$ is a divalent hydrocarbon group of 4 to 10 carbon atoms which may be separated by an oxygen atom. The divalent hydrocarbon group is exemplified by those listed above for $R^2$, but having 4 to 10 carbon atoms. Typical examples of $R^5$ are pentylene, hexylene, decylene, and ethylenoxyethylene.

Illustrative, non-limiting examples of the organosilicon compound are given below.

The organosilicon compound of the invention can be prepared by reacting an amino-bearing compound of formula (2) with an aqueous solution of alkali hypochlorite, separating an aqueous layer from the reaction solution, and further reacting the reaction product with a mercapto-bearing organosilicon compound of formula (3).

(2)

(3)

Herein, $R^1$, $R^2$, $R^3$, $R^4$ and n are as defined above. When $R^3$ and $R^4$ bond together to form an alicyclic structure, the compound of formula (2) is represented by the following general formula (2'):

(2')

wherein $R^5$ is as defined above.

Illustrative, non-limiting examples of the compound of formula (2) are given below.

$CH_3NH_2$,
$CH_3CH_2NH_2$,
$CH_3CH_2CH_2NH_2$,
$CH_3CH_2CH_2CH_2NH_2$, n-hexylamine,
cyclohexylamine,
dicyclohexylamine,
phenylamine,
benzylamine,
piperidine,
morpholine,
pyrrolidine,
azepine,
perhydroazepine.

Illustrative, non-limiting examples of the compound of formula (3) are given below.

$(CH_3O)_3Si(CH_2)_3SH$,
$(CH_3CH_2O)_3SiCH_2SH$,
$(CH_3CH_2O)_3Si(CH_2)_3SH$,
$(CH_3CH_2CH_2O)_3SiCH_2SH$,
$(CH_3CH_2CH_2O)_3Si(CH_2)_6SH$,
$(CH_3CH_2CH_2CH_2O)_3SiCH_2SH$,
$(CH_3CH_2CH_2CH_2O)_3Si(CH_2)_6SH$,

-continued

Of these, the following are preferred for practical use.
$(CH_3O)_3Si(CH_2)_3SH$,
$(CH_3CH_2O)_3Si(CH_2)_3SH$, The alkali hypochlorite is preferably sodium hypochlorite or potassium hypochlorite. These are commercially available in aqueous solution form.

In the step of reacting the amino-bearing compound of formula (2) with an alkali hypochlorite aqueous solution, an extracting solvent may or may not be used. Examples of the extracting solvent used herein include hydrocarbons such as pentane, hexane, heptane, octane, benzene, toluene and xylene, alcohols such as butanol and octanol, ethers such as dibutyl ether, tetrahydrofuran, and dioxane, ketones such as methyl ethyl ketone and methyl isobutyl ketone, esters such as ethyl acetate, and amides such as dimethylformamide. Of these, aliphatic hydrocarbons such as pentane, hexane, heptane, and octane are preferred because they are unlikely to take up water.

In this step, the reaction temperature is generally about 0° C. to about 100° C., preferably about 20° C. to about 80° C., and the reaction time is generally about 5 minutes to about 10 hours.

The amino-bearing compound of formula (2) and the alkali hypochlorite are used in any desired molar ratio as long as the amino-bearing compound is excessive. An appropriate molar ratio of amino-bearing compound to alkali hypochlorite is from 1.01/1 to 3/1.

Next, an aqueous layer is separated from the reaction solution. The reaction product is then reacted with a mercapto-bearing organosilicon compound of the general formula (3). A dehydrochlorination agent may or may not be added in this step. As the dehydrochlorination agent used in this step, the compound of formula (2) may be added again. Alternatively, another dehydrochlorination agent, for example, a tertiary amine compound, typically triethylamine is used. The amount of the dehydrochlorination agent added is in excess of the moles of the mercapto-bearing organosilicon compound. The molar ratio of dehydrochlorination agent to mercapto-bearing organosilicon compound is preferably from about 1/1 to about 4/1, and especially about 2/1.

A solvent may or may not be used in the reaction. Examples of the reaction solvent include hydrocarbons such as pentane, hexane, heptane, octane, benzene, toluene and xylene, alcohols such as methanol, ethanol, butanol and octanol, ethers such as dibutyl ether, tetrahydrofuran, and dioxane, ketones such as methyl ethyl ketone and methyl isobutyl ketone, esters such as ethyl acetate, and amides such as dimethylformamide.

The reaction temperature is not critical although a temperature of about 20° C. to about 120° C. is preferred. The reaction is continued until the mercapto compound disappears, for example, for about 30 minutes to about 15 hours.

The mercapto-bearing organosilicon compound is preferably added in such amounts that the molar ratio of alkali hypochlorite to mercapto-bearing organosilicon compound may range from about 0.8/1 to about 1.5/1. If the amount of the mercapto-bearing organosilicon compound added is greater than this range, a more amount of disulfide compounds may form as by-products.

It is noted that the organosilicon compound of formula (1) can also be synthesized by reacting a compound of formula (3) with chlorine to form a compound of the general formula (4) shown below, and effecting dehydrochlorination reaction between the compound of formula (4) and a compound of formula (2). Since this process uses highly toxic chlorine, the aforementioned process is desirable.

The organosilicon compounds of the invention are useful as interfacial binders between inorganic materials such as silica, aluminum hydroxide and talc and organic materials such as thermosetting resins, thermoplastic resins and rubber, adhesion modifiers for organic resins and rubber, primers, etc.

EXAMPLE

Examples of the invention are given below by way of illustration and not by way of limitation.

Example 1

A 1-liter separable flask equipped with a nitrogen feed tube, thermometer, Dimroth condenser and dropping funnel was charged with 73 g (1 mol) of t-butylamine and 150 g of heptane. To the solution at 25° C., 360 g (0.507 mol) of 5% sodium hypochlorite aqueous solution was added dropwise over 10 minutes. After the completion of dropwise addition, the solution was ripened for one hour.

The reaction solution was transferred to a separatory funnel, through which an aqueous solution as the lower layer was removed, leaving 235 g of a colorless clear heptane solution. The solution was combined with 73 g (1 mol) of t-butylamine and 200 g of heptane and heated to 68° C.

To the solution, 107 g (0.45 mol) of 3-mercaptopropyltriethoxysilane represented by the formula: $(CH_3CH_2O)_3Si(CH_2)_3SH$ was slowly added dropwise. The reaction was exothermic and the temperature rose to 73° C. during the addition. After the completion of dropwise addition, the solution was ripened for one hour at 73° C.

At the end of ripening, the end product was purified by distillation. At a boiling point of 124° C./3 mmHg, 56.7 g of a colorless clear liquid was collected. This liquid had a viscosity of 3.73 centistokes at 25° C. and a refractive index of 1.4442 at 25° C. On gas chromatography analysis, it was found to be 95.6% pure.

Figure 1:
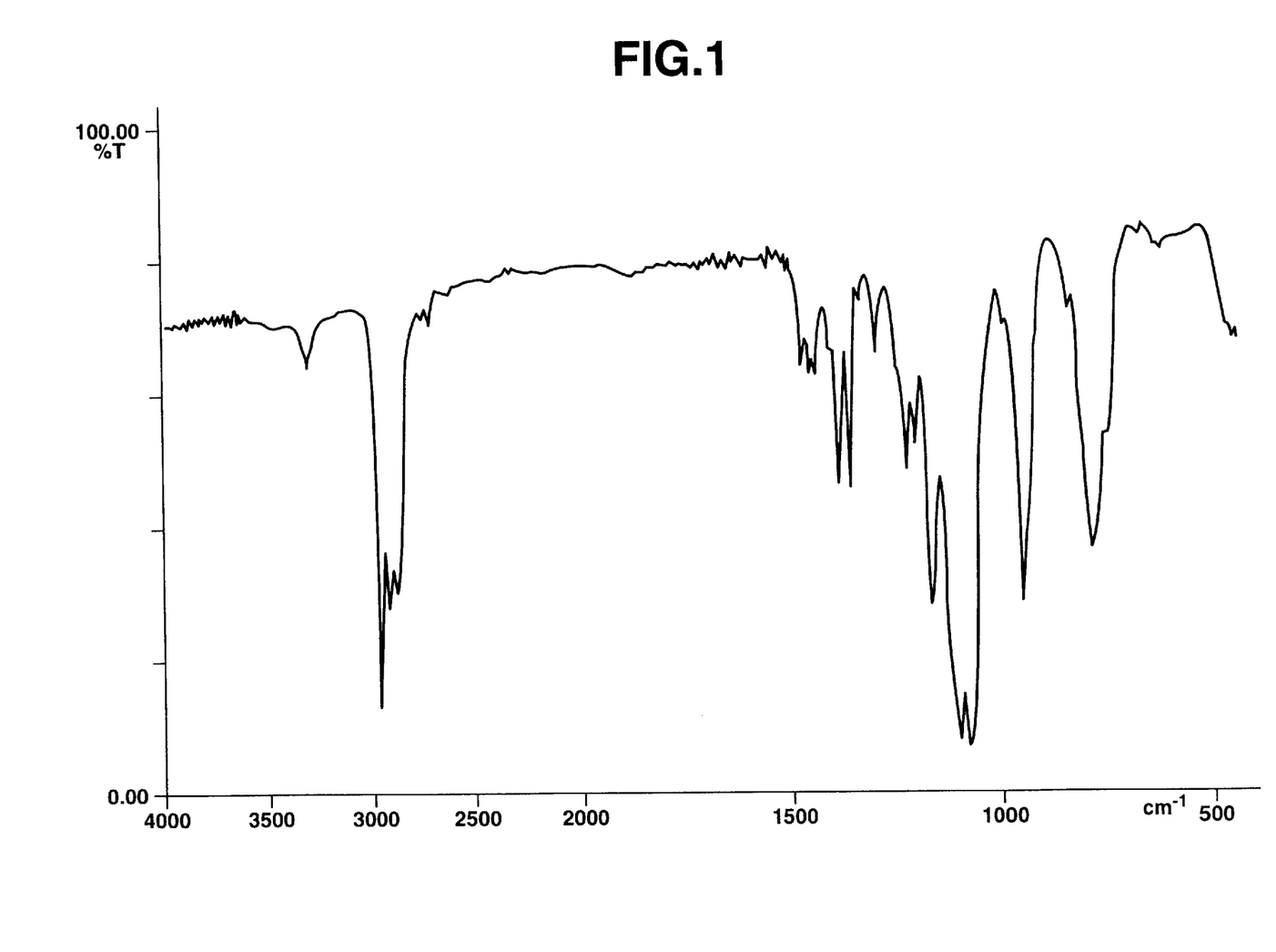
FIG. 1 is an IR absorption spectrum of the compound of Example 1.
Figure 2:
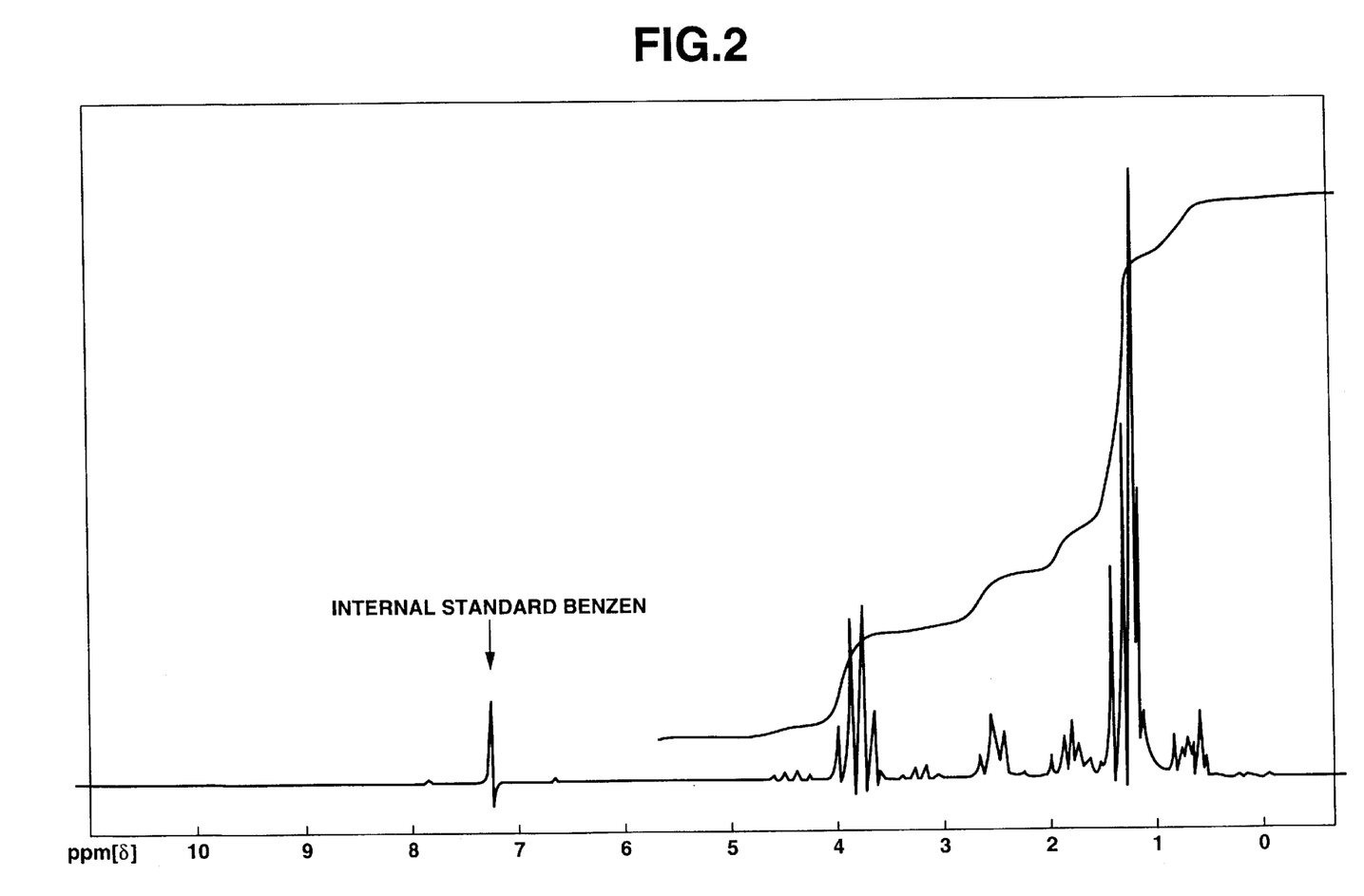
FIG. 2 is a 1H NMR spectrum of the compound of Example 1.
Figure 3:
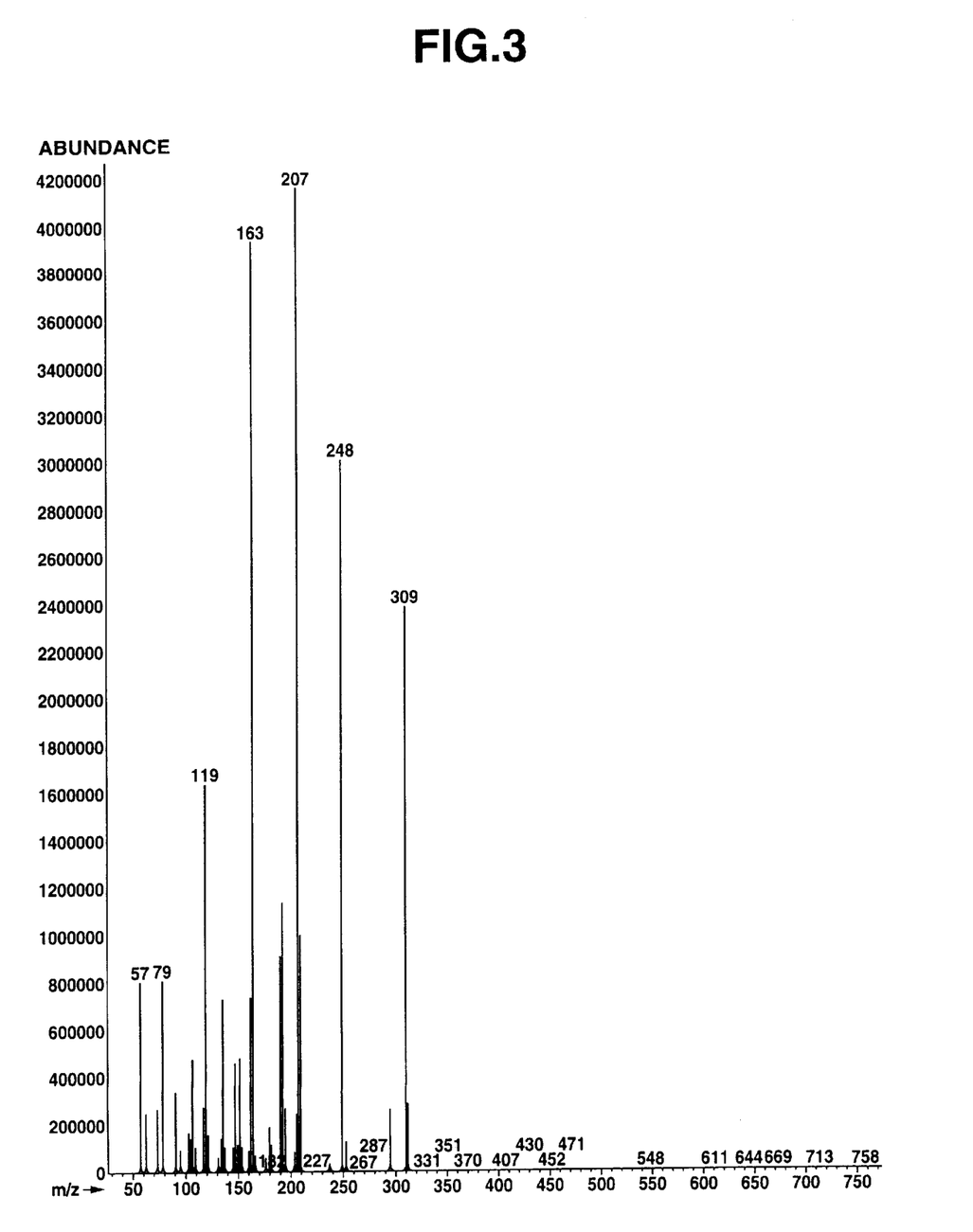
FIG. 3 is a GC-MS spectrum of the compound of Example 1.

The product was examined by infrared absorption spectroscopy, 1H NMR spectroscopy, and GC-MS analysis, with the results shown in the diagrams of FIGS. 1, 2 and 3, respectively. The product was thus identified to be N-t-butyl-3-triethoxysilylpropylsulfenamide represented by the following formula.

$$(CH_3CH_2O)_3Si\text{---}(CH_2)_3\text{---}SNHC(CH_3)_3$$

Example 2

A flask as used in Example 1 was charged with 87 g (1 mol) of morpholine and 150 g of heptane. To the solution at 25° C., 360 g (0.507 mol) of 5% sodium hypochlorite aqueous solution was added dropwise over 10 minutes. After the completion of dropwise addition, the solution was ripened for 30 minutes.

The reaction solution was transferred to a separatory funnel, through which an aqueous solution as the lower layer was removed, leaving 210 g of a colorless clear heptane solution. To the solution were added 87 g (1 mol) of morpholine and 100 g of toluene.

To the solution at 25° C., 107 g (0.45 mol) of 3-mercaptopropyltriethoxysilane represented by the formula: $(CH_3CH_2O)_3Si(CH_2)_3SH$ was slowly added dropwise. The reaction was exothermic and the temperature rose to 70° C. during the addition. After the completion of dropwise addition, the solution was ripened for one hour at 65° C.

At the end of ripening, the end product was purified by distillation. At a boiling point of 144° C./3 mmHg, 62.1 g of a colorless clear liquid was collected. This liquid had a viscosity of 5.29 centistokes at 25° C., a refractive index of 1.4610 at 25° C., and a specific gravity of 1.043 at 25° C. On gas chromatography analysis, it was found to be 98.8% pure.

Figure 4:
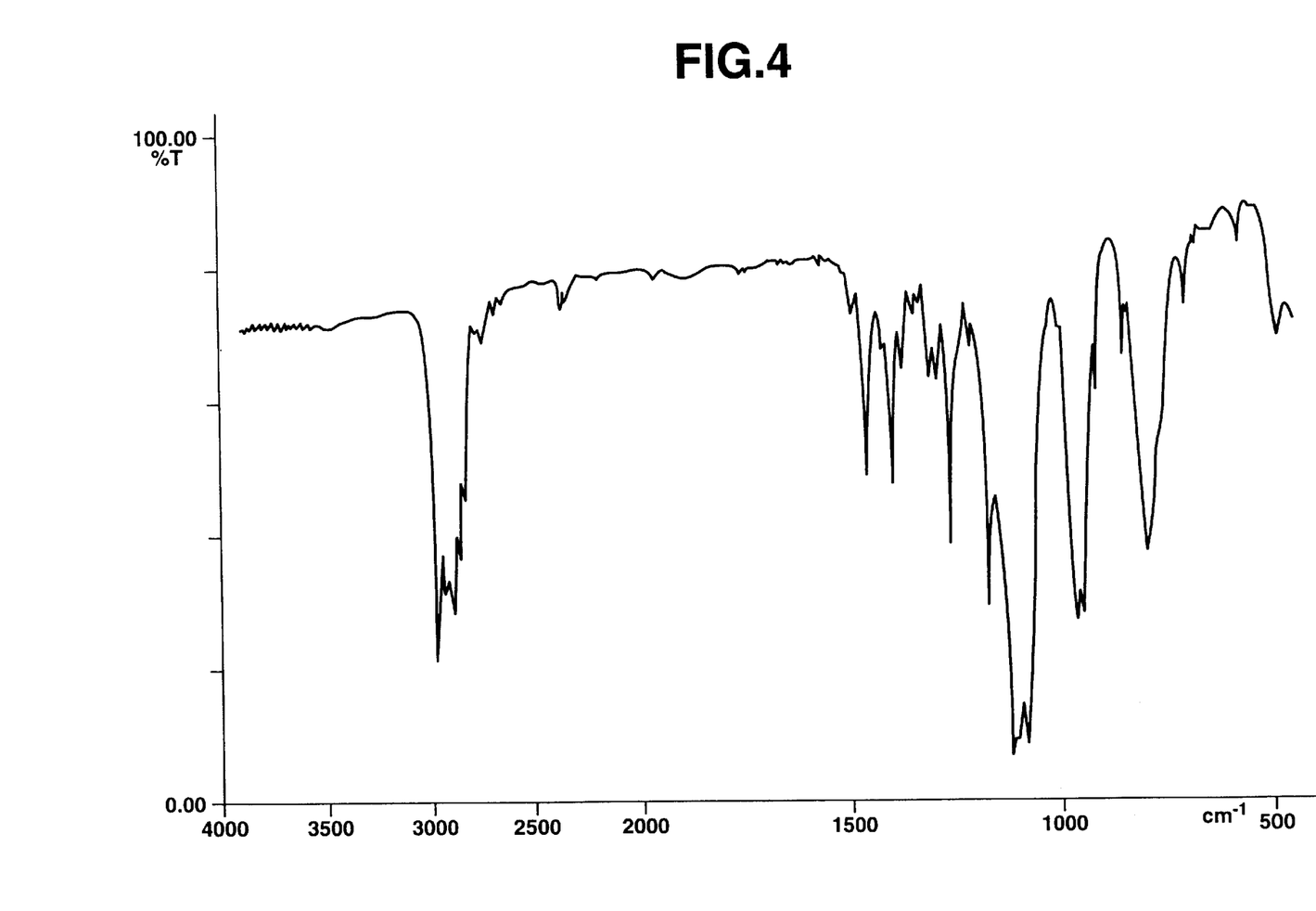
FIG. 4 is an IR absorption spectrum of the compound of Example 2.
Figure 5:
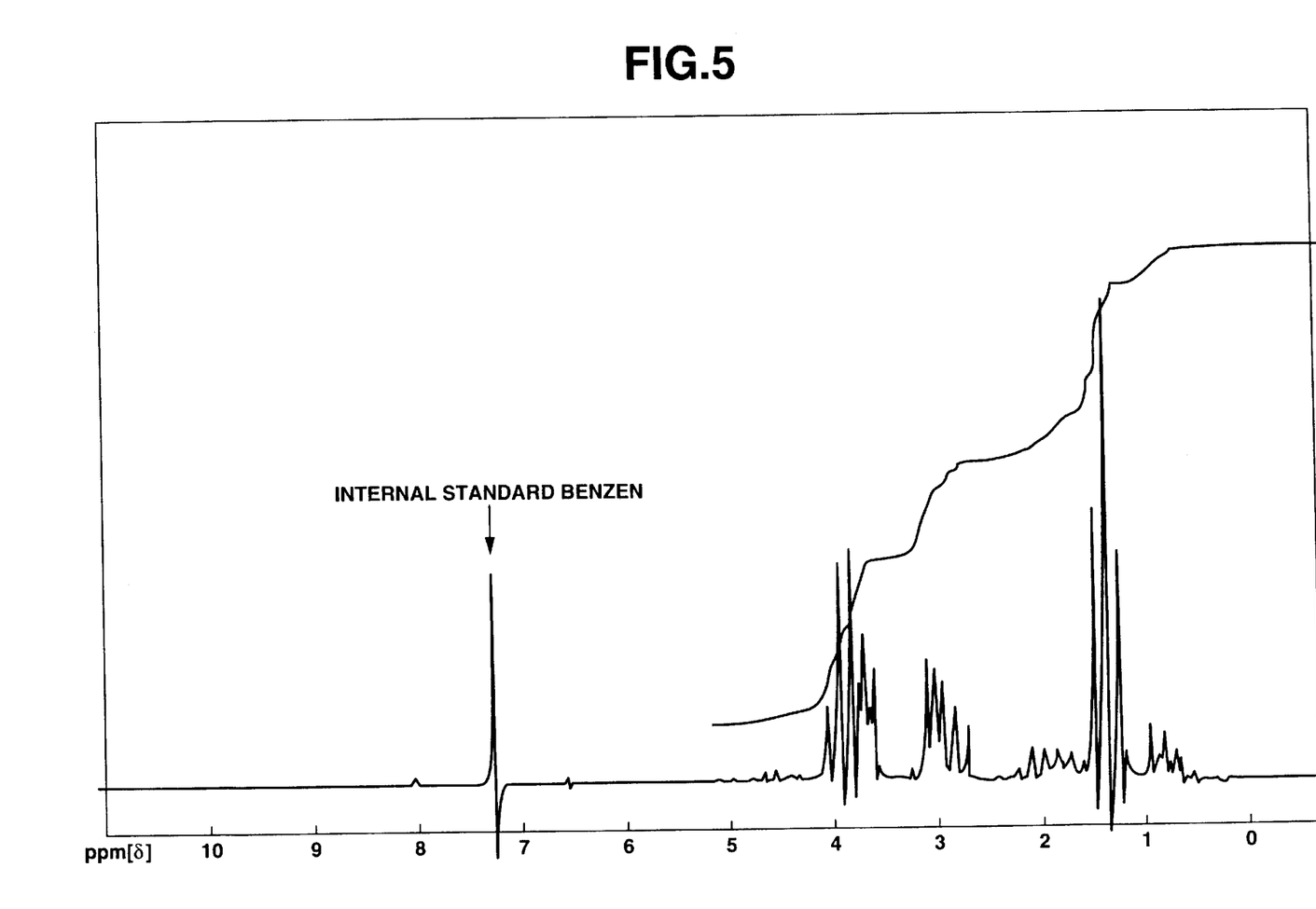
FIG. 5 is a 1H NMR spectrum of the compound of Example 2.
Figure 6:
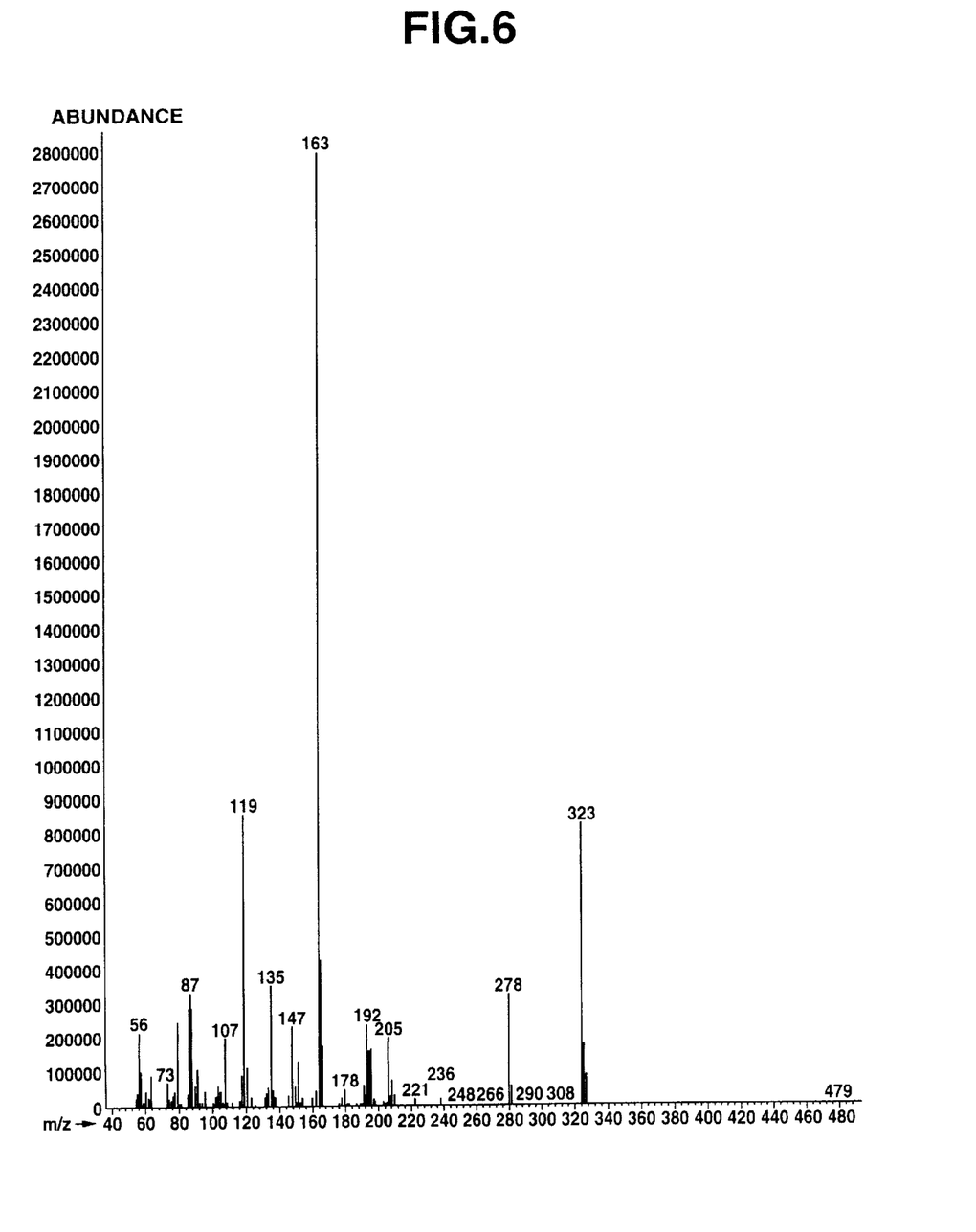
FIG. 6 is a GC-MS spectrum of the compound of Example 2.

The product was examined by IR absorption spectroscopy, 1H NMR spectroscopy, and GC-MS analysis, with the results shown in the diagrams of FIGS. 4, 5 and 6, respectively. The product was thus identified to be N-oxydiethylene-3-triethoxysilylpropylsulfenamide represented by the following formula.

$$(CH_3CH_2O)_3Si\text{---}(CH_2)_3\text{---}SN(CH_2CH_2)_2O$$

Examples 3–6

Following the procedure of Example 1, synthesis was carried out using the compounds shown in Table 1.

TABLE 1

| | Amine compound | Mercapto-bearing organosilicon compound |
| --- | --- | --- |
| Example 3 | morpholine | $(CH_3O)_3Si(CH_2)_3SH$ |
| Example 4 | cyclohexylamine | $(CH_3CH_2O)_3Si(CH_2)_3SH$ |
| Example 5 | dicyclohexylamine | $(CH_3CH_2O)_3Si(CH_2)_3SH$ |
| Example 6 | diisopropylamine | $(CH_3CH_2O)_2Si(CH_3)(CH_2)_3SH$ |

The end compounds were examined by IR absorption spectroscopy and 1H NMR spectroscopy to confirm their structure. The structural formulas of the end compounds are given below.

Example 3

$$(CH_3O)_3Si\text{---}(CH_2)_3\text{---}SN(CH_2CH_2)_2O \text{ (morpholino)}$$

Example 4

$$(CH_3CH_2O)_3Si\text{---}(CH_2)_3\text{---}SNH(C_6H_{11})$$

Example 5

$$(CH_3CH_2O)_3Si\text{---}(CH_2)_3\text{---}SN(C_6H_{11})_2$$

Example 6

$$(CH_3CH_2O)_2Si(CH_3)\text{---}(CH_2)_3\text{---}SN[CH(CH_3)_2]_2$$

There have been described organosilicon compounds having organooxysilyl and sulfenamide groups, which are useful as interfacial binders between inorganic materials and organic materials (e.g., thermosetting resins, thermoplastic resins and rubber), adhesion modifiers for organic resins and rubber, primers, etc. When the organosilicon compound is used in such an application involving mixing of a resin or rubber with an inorganic material, there is no likelihood that the resin or rubber cure during mixing.

Japanese Patent Application No. 11-004917 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An organosilicon compound of the following general formula (1):

$$(R^1O)_n Si(CH_3)_{3-n}\text{---}R^2\text{---}S\text{---}NR^3R^4 \tag{1}$$

wherein $R^1$ is a monovalent hydrocarbon group of 1 to 4 carbon atoms, $R^2$ is a divalent hydrocarbon group of 1 to 10 carbon atoms, $R^3$ is hydrogen or a monovalent hydrocarbon group of 1 to 10 carbon atoms, $R^4$ is a monovalent hydrocarbon group of 1 to 10 carbon atoms, or $R^3$ and $R^4$, taken together with the nitrogen atom, form an alicyclic structure of 4 to 10 carbon atoms which may be separated by an oxygen atom, and n is equal to 1, 2 or 3.

2. A method for preparing an organosilicon compound of the following general formula (1):

(1)

wherein $R^1$ is a monovalent hydrocarbon group of 1 to 4 carbon atoms, $R^2$ is a divalent hydrocarbon group of 1 to 10 carbon atoms, $R^3$ is hydrogen or a monovalent hydrocarbon group of 1 to 10 carbon atoms, $R^4$ is a monovalent hydrocarbon group of 1 to 10 carbon atoms, or $R^3$ and $R^4$, taken together with the nitrogen atom, form an alicyclic structure of 4 to 10 carbon atoms which may be separated by an oxygen atom, and n is equal to 1, 2 or 3, said method comprising the steps of:

reacting an amino-bearing compound of the following general formula (2):

(2)

wherein $R^3$ and $R^4$ are as defined above, with an alkali hypochlorite aqueous solution, separating an aqueous layer from the resulting reaction product, further reacting the reaction product with a mercapto-bearing organosilicon compound of the following general formula (3):

(3)

wherein $R^1$, $R^2$ and n are as defined above.

* * * * *